USom008168942B2

(12) United States Patent
Sumiyoshi

(10) Patent No.: US 8,168,942 B2
(45) Date of Patent: May 1, 2012

(54) CHROMATOGRAPH MASS SPECTROMETER

(75) Inventor: Takashi Sumiyoshi, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 688 days.

(21) Appl. No.: 12/281,698

(22) PCT Filed: Mar. 7, 2006

(86) PCT No.: PCT/JP2006/304371
§ 371 (c)(1),
(2), (4) Date: Sep. 4, 2008

(87) PCT Pub. No.: WO2007/102201
PCT Pub. Date: Sep. 13, 2007

(65) Prior Publication Data
US 2009/0008542 A1  Jan. 8, 2009

(51) Int. Cl.
B01D 59/44 (2006.01)
(52) U.S. Cl. ........................................ 250/281; 250/282
(58) Field of Classification Search .................. None
See application file for complete search history.

(56) References Cited

U.S. PATENT DOCUMENTS

| 7,269,994 B2* | 9/2007 | Umemura | 73/23.37 |
| 7,759,130 B2* | 7/2010 | Oda et al. | 436/173 |
| 2003/0213908 A1* | 11/2003 | Umemura | 250/292 |
| 2005/0211892 A1* | 9/2005 | Shimomura | 250/282 |
| 2005/0252275 A1* | 11/2005 | Kita et al. | 73/23.34 |
| 2006/0101898 A1* | 5/2006 | Umemura | 73/23.37 |
| 2007/0134806 A1* | 6/2007 | Oda et al. | 436/173 |

FOREIGN PATENT DOCUMENTS

| DE | 19845699 C1 | 12/1999 |
| GB | 2404194 A | 1/2005 |
| JP | 4-294271 A | 10/1992 |
| JP | 8-102282 A | 4/1996 |
| JP | 08102282 A * | 4/1996 |
| JP | 9-318599 A | 12/1997 |
| JP | 2003-172726 A | 6/2003 |
| JP | 2003172726 A * | 6/2003 |
| JP | 2006-010323 A | 1/2006 |
| JP | 2006010323 A * | 1/2006 |

OTHER PUBLICATIONS

European Search Reported dated Oct. 28, 2010 for corresponding European Patent Application No. 06715341.1.

(Continued)

Primary Examiner — Jack Berman
Assistant Examiner — Andrew Smyth
(74) Attorney, Agent, or Firm — Sughrue Mion, PLLC

(57) ABSTRACT

In a chromatograph mass spectrometer capable of defining an appropriate measurement time range and selectively performing a scan measurement, selected ion monitoring (SIM) measurement or simultaneous scan/SIM measurement in that time range, a total ion chromatogram 51 obtained by a scan measurement of a standard sample and a previously-created compound table 52 are displayed on the screen of a display unit in the process of setting parameters in a measurement condition table. An operator selects a compound that should undergo the simultaneous scan/SIM measurement, then places a checkmark in an appropriate check box in the compound table 52, and finally clicks the "Auto-Create" button 54. Then, a measurement time range for the selected compound is defined by adding a time span before and after the retention time of that compound, respectively, and a measurement condition table 53 is automatically created and displayed on the screen. This table includes instructions for performing a simultaneous scan/SIM measurement at specific mass-to-charge ratios characteristic of the selected compound during the aforementioned measurement time range.

12 Claims, 5 Drawing Sheets

OTHER PUBLICATIONS

Dalluge J et al: "Unravelling the composition of very complex samples by comprehensive gas chromatography coupled to time-of-flight mass spectrometry—Cigarette smoke", Journal of Chromatography, Elsevier Science Publishers B.V, NL, vol. 974, No. 1-2, Oct. 18, 2002, pp. 169-184, XP004387548, ISSN: 0021-9673, DOI: DOI:10 .1016/S0021-9673(02)01384-5.

* cited by examiner

|   | Compound Name | Retention Time (min) | m/z 1 | m/z 2 | m/z 3 | m/z 4 |
|---|---|---|---|---|---|---|
| 1 | Component A | 10 | 200 | 250 |  |  |
| 2 | Component B | 12 | 100 | 200 | 300 | 400 |
| 3 | Component C | 18 | 150 | 160 |  |  |
| 4 | Component D | 20 | 200 | 300 |  |  |

|   | Finish Time (min) | m/z 1 | m/z 2 | m/z 3 | m/z 4 | ------- |
|---|---|---|---|---|---|---|
| 1 | 11.5 |  |  |  |  |  |
| 2 | 13.5 | 100 | 200 | 300 | 400 |  |
| 3 | 17.5 |  |  |  |  |  |
| 4 | 18.5 | 150 | 160 |  |  |  |
| 5 | 22 |  |  |  |  |  |

| | Start Time (min) | Finish Time (min) | Method | m/z starting | m/z finishing | m/z 1 | m/z 2 | m/z 3 | m/z 4 | ----- |
|---|---|---|---|---|---|---|---|---|---|---|
| 1 | 6 | 20 | Scan | 100 | 400 | | | | | |

⇒

(b)

| | Start Time (min) | Finish Time (min) | Method | m/z starting | m/z finishing | m/z 1 | m/z 2 | m/z 3 | m/z 4 | ----- |
|---|---|---|---|---|---|---|---|---|---|---|
| 1 | 6 | 11 | Scan | 100 | 400 | | | | | |
| 2 | 11 | 13 | Scan | 100 | 400 | | | | | |
| 3 | 11 | 13 | SIM | | | 100 | 200 | 300 | 400 | |
| 4 | 13 | 20 | Scan | 100 | 400 | | | | | |

CHROMATOGRAPH MASS SPECTROMETER

TECHNICAL FIELD

The present invention relates to a chromatograph mass spectrometer, such as a gas chromatograph/mass spectrometer (GC/MS) or liquid chromatograph/mass spectrometer (LC/MS), in which a chromatograph is combined with a mass spectrometer. Specifically, it relates to a chromatograph mass spectrometer capable of simultaneously collecting data by a scan measurement and selected ion monitoring measurement.

BACKGROUND ART

The measurement methods of chromatograph mass spectrometers such as the GC/MS or LC/MS can be classified into two modes, i.e. the scan measurement and the selected ion monitoring (SIM) measurement. In the scan measurement mode, the mass spectrometer scans the mass-to-charge ratios (m/z) of ions to be analyzed over a predetermined mass range in order to detect all varieties of ions included in the aforementioned mass range. This mode of measurement is particularly useful in the case where the mass-to-charge ratio of the component of interest is unknown, as in the case of a qualitative analysis of an unknown sample. However, this mode is not suitable for quantitative analyses since the signal-to-noise (S/N) ratio of the resultant mass chromatogram is rather low. On the other hand, in the SIM measurement mode, one or more ions with previously-specified mass-to-charge ratios are selectively detected in a time-sharing manner. This mode of measurement is useful in the case where the quantity of a known kind of substance should be measured with high sensitivity. However, this mode is not suitable for qualitative analyses since it detects only the ions having specific mass-to-charge ratios.

As explained previously, the scan measurement and the SIM measurement are complementary to each other. To utilize the characteristics of these methods, a simultaneous scan/SIM measurement method has been proposed (for example, refer to Patent Document 1), in which the scan measurement and the SIM measurement are simultaneously performed in a specified time range. This method is capable of simultaneously producing both a mass spectrum for a qualitative mass analysis and a chromatogram with a high S/N ratio for a quantitative analysis of a target ion, by one cycle of analyzing operations.

Although the simultaneous scan/SIM measurement method is a useful technique, the method causes the problem that, if this mode of measurement is performed on a large number of compounds including the compounds that do not actually need to undergo the simultaneous scan/SIM measurement, then there will be too large an amount of ions introduced into the detector per unit time, which deteriorates the detection sensitivity. Accordingly, it is often the case that the simultaneous scan/SIM measurement is only performed on the compounds for which a mass spectrum with an adequately high S/N ratio cannot be created by the normal scan measurement, whereas only the scan measurement is performed on the other compounds. Therefore, in advance of the measurement, it is necessary to select target compounds that should undergo the simultaneous scan/SIM measurement, and to specify mass-to-charge ratios at which the measurement should be performed.

In the case of a conventional chromatograph mass spectrometer, this measurement is typically performed as follows. First, with the apparatus in the scan mode, an operator performs a preliminary measurement of a standard sample containing known components to obtain a chromatogram (total ion chromatogram) of the sample. This chromatogram is used to determine whether or not each of the target compounds (i.e. the compounds to be quantitatively measured) can be detected with an adequately high S/N ratio. Based on the determination results, the operator selects target compounds that should be subjected to the simultaneous scan/SIM measurement. Subsequently, the operator specifies the time range for the simultaneous scan/SIM measurement and the mass-to-charge ratios at which the SIM measurement should be performed within the time range so that the peaks of the selected target compounds will be covered by the measurement.

Subsequently, the operator performs a predetermined operation on an input unit of the apparatus to display a measurement condition table, as shown in FIG. 7. In this table, the operator enters, for each measurement time range, the start time, finish time, measurement mode (scan or SIM), mass range (i.e. the starting and finishing values of m/z) for the scan measurement or mass-to-charge ratios for the SIM measurement, and other numerical values. After the necessary items of information are completely set, the operator fixes the settings. According to the measurement conditions thus specified, the apparatus performs the measurement of a standard sample for calibration and then the measurement of an unknown sample.

In the example of FIG. 7(a), a scan measurement is performed over a mass range from 100 to 400 for a period of time from 6 to 20 minutes in terms of the time elapsed from the measurement start time (zero minutes). On the other hand, in the example of FIG. 7(b), a scan measurement is initially performed over a mass range from 100 to 400 for a period of time from 6 to 11 minutes in terms of the time elapsed from the measurement start time (the first row of the table). Next, from 11 to 13 minutes, the scan measurement is performed over the mass range from 100 to 400 (the second row of the table), with which an SIM measurement is simultaneously carried out at four mass-to-charge ratios of 100, 200, 300 and 400 (the third row of the table). Finally, from 13 to 20 minutes, the scan measurement is performed over the mass range from 100 to 400 (the fourth row of the table).

In the example of FIG. 7(b), the simultaneous scan/SIM measurement is only performed on one compound. However, in actual analyses, the sample may contain more than 100 components, in which case the number of compounds to be measured in the simultaneous scan/SIM mode accordingly increases. Starting from a simple table, like the one in FIG. 7(a) in which conditional information for a scan measurement is set for a specific measurement time range (6 to 20 minutes in the present example), if conditions for the simultaneous scan/SIM measurement of a new target compound must be added as shown in FIG. 7(b), it is necessary for the operator to add three rows to the measurement condition table and perform key operations to enter parametric values into the cells of each of the three rows. If ten components are to be added for the simultaneous scan/SIM measurement, it is necessary to add up to 30 rows to the measurement condition table and enter necessary information into these rows. Thus, if there are many components, this task will be extremely troublesome for the operator and potentially cause more input errors.

Another problem relates to the setting of a time range for the simultaneous scan/SIM measurement. The operator has to correctly set this time range when inputting numerical values into the measurement condition table. For example, suppose that a chromatogram has two components represented by two peaks whose retention times are close to each other, and a boundary of the time range for the simultaneous scan/SIM measurement is set between these two peaks. Then, the two peaks inevitably exist in the vicinity of the boundary. In this case, even a small shift of the retention time during the measurement of an unknown sample causes one peak of the chromatogram to overlap this boundary of the time range. This situation leads to an incorrect detection of the peak and wrong calculation of the peak area, so that the quantitative analysis cannot be correctly performed. To avoid this problem, it is necessary to carefully set the time range for the simultaneous scan/SIM measurement, referring to the chromatogram obtained by the preliminary measurement of a standard sample. However, in the case of conventional apparatuses, it is difficult to precisely perform this setting since the apparatuses have no means for referring to the preliminarily obtained chromatogram on the same screen when setting the time range for the simultaneous scan/SIM measurement as described earlier.

Patent Document 1: Japanese Unexamined Patent Application Publication No. H08-102282

DISCLOSURE OF THE INVENTION

Problem to be Solved by the Invention

The present invention has been developed to solve the previously-described problems, and an objective of the invention is to provide a chromatograph mass spectrometer capable of efficiently and correctly setting measurement conditions for a simultaneous scan/SIM measurement in a simple manner.

Means for Solving the Problems

To solve the aforementioned problems, the present invention provides a chromatograph mass spectrometer having a chromatograph section in which sample components are separated in a temporal direction and a mass spectrometer section in which the sample components are sequentially subjected to a mass analysis, the mass spectrometer section being capable of selectively performing a scan measurement in which the mass-to-charge ratio is continuously and repeatedly scanned over a predetermined mass range, a selected ion monitoring (SIM) measurement in which the mass-to-charge ratio is switched from one value to another in a stepwise manner, with each value maintained for a specific period of time, or a simultaneous scan/SIM measurement in which the SIM measurement is performed in the course of the scan measurement, and the chromatograph mass spectrometer includes:

a) a display controller showing a previously-created compound table on a screen of a display unit, the compound table including a list showing the kind of each compound, the normal retention time of each compound, and one or more mass-to-charge ratios characteristic of each compound;

b) a selector for allowing an operator to select a compound that should undergo the simultaneous scan/SIM measurement, from the compound table displayed on the screen; and c) a measurement condition table creator producing a measurement condition table according to which the simultaneous scan/SIM measurement will be performed in a specified time range for each of one or more compounds selected by the selector and either the scan measurement or SIM measurement will be performed in the other time ranges, the specified time range being defined for each of the selected compounds by setting a predetermined time span before and after the retention time of the compound, respectively.

A time range for the simultaneous scan/SIM measurement generally corresponds to a section of the total ion chromatogram in which includes the peak of a known compound that should be quantitatively analyzed. Given this factor, in the chromatograph mass spectrometer according to the present invention, the display controller shows a previously-created compound table on the screen of the display unit. From this table, the operator, using the selector, selects a compound that should be measured in the simultaneous scan/SIM mode. Then, the measurement condition table creator sets a predetermined time span before and after the retention time of the selected compound, respectively, thus defining a time range for the simultaneous scan/SIM measurement including the peak of the selected compound. If more than one compound is selected, the same process is performed for each of the selected compounds. If two or more time ranges overlap each other, these time ranges can be merged into a larger, continuous time range.

In this manner, the measurement condition table creator creates a measurement condition table by automatically defining time ranges for the simultaneous scan/SIM measurement and assigning the other time ranges to, for example, a scan measurement over a predetermined mass, and displays the table, for example, on the screen of the display unit. However, the content of the automatically-created measurement condition table does not always agree with the intentions of the operator. Furthermore, the boundaries of the simultaneous scan/SIM measurement may be set at inappropriate points in time, particularly when the retention times of two or more compounds are located close to each other along a time scale. Therefore, it is preferable to provide a means for allowing the operator to later correct the automatically-created measurement condition table.

The tasks of selecting a compound that should undergo the simultaneous scan/SIM measurement and correcting the measurement condition table will be facilitated if a chromatogram (total ion chromatogram) is displayed on the same screen for reference. Accordingly, in the chromatograph mass spectrometer according to the present invention, it is preferable that the display controller show a total ion chromatogram obtained by a measurement of a standard sample or a known sample equivalent to the standard sample in a scan mode, SIM mode or simultaneous can/SIM mode, on the same screen on which the compound table and the measurement condition table are displayed.

It is preferable that the display controller show the total ion chromatogram in such a manner that one or more peaks present in the total ion chromatogram displayed on the screen are visually associated with one or more compounds listed in the compound table.

This configuration helps the operator to visually recognize the correspondence between the compounds listed in the compound table and the peaks present in the total ion chromatogram, and to determine whether another peak is present near the peak originating from a compound which is going to be selected. As a result, the selection of compounds will be more easily performed with fewer errors.

It is further preferable that the display controller superpose an indicator for visually identifying the time ranges of the scan measurement, SIM measurement and simultaneous scan/SIM measurement, on the total ion chromatogram when the measurement condition table is created. The indicator enables the operator to visually and intuitively grasp the time range of each of the measurements that have been programmed in the measurement condition table, thereby improving working efficiency and reducing operational errors.

If the aforementioned task of correcting the measurement condition table can be graphically performed on the total ion chromatogram displayed on the screen, the task will be more efficiently performed with fewer errors than in the case of deleting and rewriting numerical values in the table by key input operations. Accordingly, it is preferable that the time range of the scan measurement, SIM measurement and simultaneous scan/SIM measurement can be graphically corrected through the operation of a pointing device.

There are various selection methods available for the selector. In one possible mode, the selector provides the compound table with a check box for each compound in the compound table so that the operator can select a compound by checking an appropriate check box. According to this method, the compounds can be selected with simple operations and the selection result is visually easy to confirm.

EFFECT OF THE INVENTION

The chromatograph mass spectrometer according to the present invention greatly reduces the labor for the input operation necessary for setting measurement conditions for a simultaneous scan/SIM measurement, whereby the operator's workload is reduced and input errors are prevented. The graphical presentation of various types of information necessary for setting or correcting the measurement time range enables the operator to intuitively understand the situation and correctly set the measurement time range by simple operations. For example, even if a resultant chromatogram has two peaks located considerably close to each other, it is easy to avoid the situation where one of the boundaries of the measurement time ranges intervenes between the two peaks. Thus, the simultaneous scan/SIM measurement can be performed with higher degrees of accuracy.

BRIEF DESCRIPTION OF THE DRAWINGS

FIGS. 7(a) and 7(b) are tables illustrating a method of entering numerical values into a measurement condition table in a conventional GC/MS.

BEST MODE FOR CARRYING OUT THE INVENTION

A gas chromatograph/mass spectrometer (GC/MS) is hereinafter described as an embodiment of the present invention.

Figure 1:
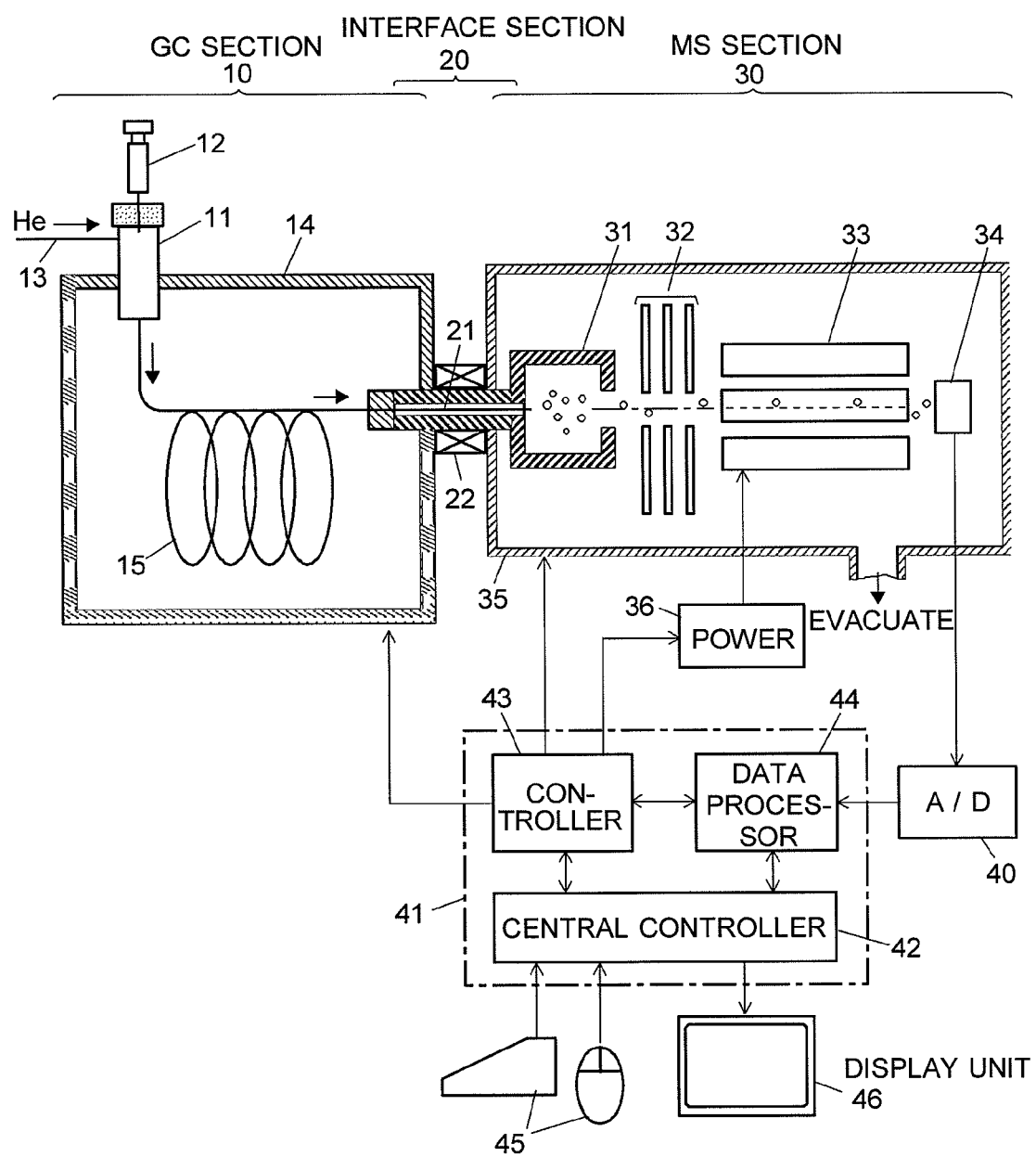
FIG. 1 is an overall configuration diagram of a GC/MS according to an embodiment of the present invention.

FIG. 1 is an overall configuration diagram of the GC/MS in the present embodiment. A gas chromatograph (GC) section 10 includes a sample-vaporizing chamber 11 at the inlet of a column 15 heated by a column oven 14 at appropriate temperatures. A carrier gas is supplied through a carrier-gas channel 13 into the sample vaporization chamber 11 at a predetermined flow rate and then flows into the column 15. In this situation, when a small quantity of liquid sample is injected from a microsyringe 12 into the sample-vaporizing chamber 11, the liquid sample becomes immediately vaporized, and the carrier gas conveys the vaporized sample ("sample gas") into the column 15. While passing through the column 15, the components of the sample gas are temporally separated and individually reach the outlet of the column 15. Then, the components enter an interface section 20, where they are drawn through a sample introduction tube 21, which is heated by a heater 22, into an ionization chamber 31 of a mass spectrometer (MS) section 30.

In the MS section 30, the sample molecules that have been introduced into the ionization chamber 31 are ionized, for example, by contact with thermions. The resultant ions are extracted from the ionization chamber 31 and converged by an ion lens 32. The converged ion beam is introduced into a space extending along the longitudinal axis of a quadrupole mass filter 33 consisting of four rod electrodes. A voltage composed of a radio-frequency voltage superposed on a DC voltage is applied from a power source 36 to the quadrupole mass filter 33, so that only the ions having a mass-to-charge ratio corresponding to the applied voltage will pass through the axially extending space and arrive at, and detected by, an ion detector 34. The ionization chamber 31, ion lens 32, quadrupole mass filter 33 and ion detector 34 are located within a vacuum container 35, which is evacuated by a vacuum pump (not shown).

The detection signals generated by the ion detector 34 are converted to digital data by an analogue-to-digital (A/D) converter 40 and sent to a data processor 44. The data processor 44 performs predetermined calculations to create a mass spectrum, mass chromatogram or total ion chromatogram, and carries out necessary analyses, such as a quantitative analysis or qualitative analysis. The operations of the blocks constituting the GC section 10, interface section 20 and MS section 30 are generally controlled by an analysis controller 43. The functions of the data processor 44 and analysis controller 43 are implemented by executing a dedicated controlling/processing software program installed on a personal computer 41. The personal computer 41 includes a central controller 42, which is responsible for basic control operations, such as the input/output control of an operation unit 45 including a keyboard or pointing device (e.g. a mouse) or the input/output control of a display unit 46. The display controller and the measurement condition table creator in the present invention are implemented as specific functions of the controlling/processing software program installed on the personal computer 41, and the selector is implemented as a function achieved by the same software program in combination with the operation unit 45.

In a measurement of an unknown sample, the present GC/MS performs the following characteristic operations:

In place of the sample gas eluted from the column 15 of the GC section 10, a gasified standard sample, which is prepared beforehand, is supplied from a standard gas supply unit (not shown) into the ionization chamber 31 of the MS section 30, and a scan-mode mass analysis is performed on this standard sample. The standard sample contains a plurality of known samples by known quantities. Based on this mass analysis, the data processor 44 creates a total ion chromatogram, in which a plurality of peaks corresponding to the known samples are present, and stores the chromatogram data into a storage unit (not shown). It is unnecessary to perform the measurement of the standard sample every time a new unknown sample is to be measured; the measurement of the standard sample can be omitted if it is known that the relevant components of the unknown sample to be quantitatively measured were also contained in a previously-measured standard sample.

Figures 4, 5, 6:
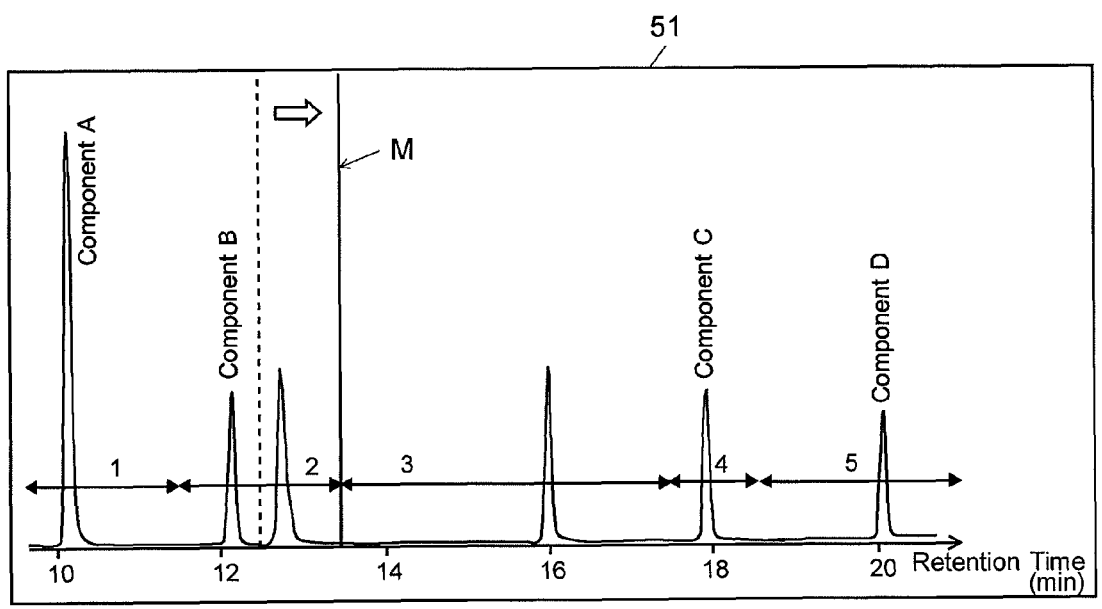
FIG. 4 is an example of a previously-created compound table.
FIG. 5 is a graph illustrating a process of correcting a boundary of the measurement time ranges.
FIG. 6 is a table illustrating a process of correcting a boundary of the measurement time ranges.

Meanwhile, a compound table as shown in FIG. 4 is created beforehand. The compound table includes a compounds list that shows the name of each compound along with various types of information such as the retention time under predetermined GC analysis conditions (the flow rate of the carrier gas in the GC section 10, the temperature profile and so on) and the mass-to-charge ratios characteristic of each compound. The compound table may be manually prepared or automatically created from the measured result of the aforementioned standard sample. It is also unnecessary to create this compound table every time a new unknown sample is to be measured; a previous version of the table can be used if the GC analysis conditions are identical.

Figure 2:
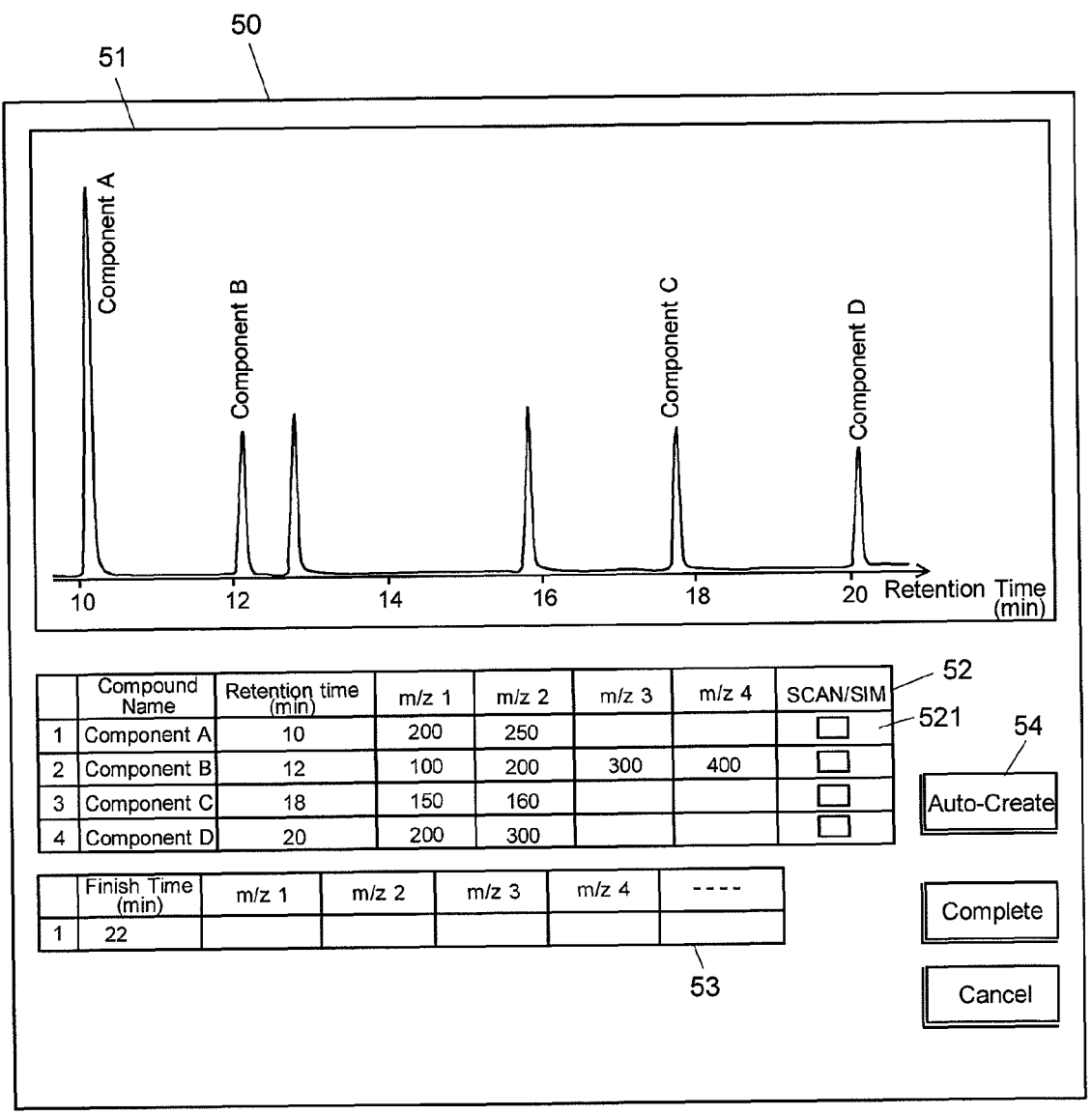
FIG. 2 is an example of a measurement condition setting screen used for setting a time range for a simultaneous scan/SIM measurement in the GC/MS according to the embodiment.

Before the measurement of an unknown sample, an operator performs a specific operation on the operation unit 45. In response to this operation, the analysis controller 43 initiates a wizard, which displays a measurement condition setting screen 50, as shown in FIG. 2, on the screen of the display unit 46. The measurement condition setting screen 50 includes a total ion chromatogram 51 obtained by a preliminary measurement of a standard sample, a compound table 52 (already mentioned), and a measurement condition table 53. As shown, the total ion chromatogram 51 has a compound name labeled in the vicinity of a peak only in the case where the compound corresponding to that peak is found in the compound table 52, whereas the other peaks that do not have corresponding compounds in the compound table 52 are unlabeled. The purpose of this presentation is to clearly show the correspondence between the compounds listed in the compound table 52 and the peaks in the chromatogram. There are many other presentation methods. For example, it is possible that the compound name of a peak is surrounded by a rectangular frame if the peak has the corresponding compound listed in the compound table 52, whereas no such frame is given to the other peaks that have no corresponding compounds listed in the compound table 52. The compound condition table 53 in FIG. 2 is in an initial state in which only the finish time is specified. This means that a scan measurement covering a specific mass range will be continued until the finish time. Alternatively, the measurement condition table 53 may initially be prepared so that an SIM measurement will be performed at specific mass-to-charge ratios.

While checking the position of each peak in the total ion chromatogram, the operator selects one or more compounds that should undergo the simultaneous scan/SIM measurement, and checks an appropriate check box 521 in the far right column of the compound table 52. It is hereby assumed that two compounds B and C should be subjected to the simultaneous scan/SIM measurement. After necessary checkmarks have been placed, the operator clicks the "Auto-Create" button 54 with a pointing device (e.g. a mouse). Then, the central controller 42 notifies the analysis controller 43 of the clicking operation. Upon receiving this notification, the analysis controller 43 determines the retention time of each of the selected components and defines a measurement time range by setting a predetermined time span before and after the retention time, respectively. Thus, a time range for the simultaneous scan/SIM measurement is defined for each of the selected components. The aforementioned time span can be arbitrarily determined by the operator, e.g. ±0.5 minutes or ±1 minutes. It is also possible that the time spans before and after the retention time have different lengths.

Figure 3:
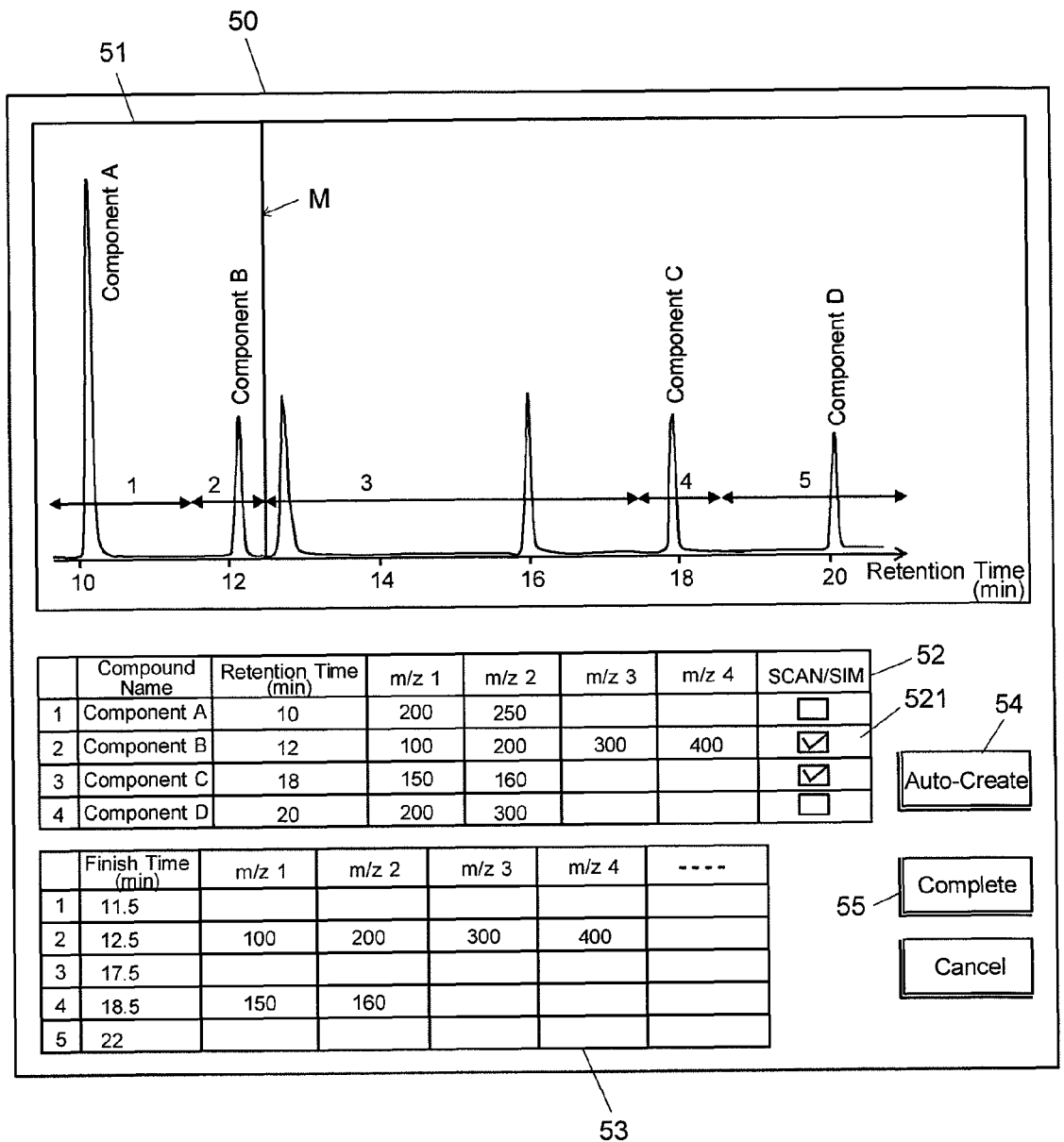
FIG. 3 is a version of the measurement condition setting screen in FIG. 2, which is displayed after the measurement condition table has been automatically created.

For example, suppose that the time spans are ±0.5 minutes. For the component B having a retention time of 12 minutes, setting a time span of 0.5 minutes before and after the retention time results in a time range of 11.5 to 12.5 minutes for the simultaneous scan/SIM measurement. Similarly, for the component C with a retention time of 18 minutes, a time range of 17.5 to 18.5 minutes is assigned to the simultaneous scan/SIM measurement. It is also assumed that the mass-to-charge ratios at which the SIM measurement should be performed during the simultaneous scan/SIM measurement are as specified in the compound table. Accordingly, the measurement on the component B will be performed at mass-to-charge ratios of 100, 200, 300 and 400, and the measurement on the component C at mass-to-charge ratios 150 and 160. Based on these conditions, a measurement condition table is automatically created, and the measurement condition setting screen 50 is updated as shown in FIG. 3. That is to say, the measurement condition table 53 in the updated version includes information about the simultaneous scan/SIM measurement, and the time-range indicators are superposed on the total ion chromatogram 51, each indicator corresponding to each row of the measurement condition table 53. In the measurement condition table 53 shown in FIG. 3, for every row in which one or more mass-to-charge ratios are specified, a SIM measurement should be performed at the specified mass-to-charge ratios along with the scan measurement, and the simultaneous measurements should start from the finish time specified in the preceding row.

Accordingly, the measurement process according to the measurement condition table 53 shown in FIG. 3 will be as follows: Initially, with the measurement start time of the preliminary measurement data of the standard sample indicated as the start time, a scan measurement is performed over a predetermined mass range until 11.5 minutes have elapsed (the first row of the measurement condition table 53). Next, from 11.5 to 12.5 minutes, the scan measurement is performed over the same mass range, simultaneously with an SIM measurement at the four mass-to-charge ratios of 100, 200, 300 and 400 (the second row of the measurement condition table 53). Then, from 12.5 to 17.5 minutes, the scan measurement is performed over the same mass range (the third row of the measurement condition table 53). In the following period of 17.5 to 18.5 minutes, the scan measurement is performed over the same mass range, simultaneously with the SIM measurement at the two mass-to-charge ratios of 150 and 160 (the fourth row of the measurement condition table 53). Finally, from 18.5 to 22 minutes, the scan measurement is performed over the same mass range (the fifth row of the measurement condition table 53).

As just described, the measurement condition table can be created with simple input operations. However, it is not always the case that the automatically-created measurement condition table can be used intact. For example, in FIG. 3, a boundary of the measurement time range is located between the peak originating from the component B and another peak originating from component E (this name is not labeled in FIG. 3) that follows the component B, and these two peaks are considerably close to each other in the total ion chromatogram. Under this condition, if the retention time of the component B has shifted during the measurement of an unknown sample containing the component B, the elution of the peak of the component B may take place across the boundary of the measurement time range. If this occurs, it will be impossible to correctly detect the peak of the component B and calculate the peak area, so that the quantitative analysis will be unfavorably affected. To avoid this situation, the operator can easily correct or modify the measurement time range in the automatically-created measurement condition table by the following procedure when such a correction or modification is necessary.

In the process of correcting the measurement time range, the row of the measurement condition table 53 that includes the measurement time range to be changed is initially clicked with the pointing device. For example, suppose that the second row of the measurement condition table 53 has been clicked. Then, a marker M indicating the finish time specified in the clicked row appears in the total ion chromatogram 51 (refer to FIGS. 3 and 5). Using the pointing device, this marker M can be selected, moved to an appropriate position and unselected. As a result, the measurement time range will be expanded or reduced to the point in time corresponding to the new position of the marker M. For example, if the marker M is moved from 12.5 to 13.5 minutes along the time scale as shown in FIG. 5, the arrows indicating the measurement time ranges accordingly change their lengths. Simultaneously, the relevant parameter in the measurement condition table 53 (i.e. the finish time in the second row) also changes from 12.5 to 13.5 minutes. Thus, the operation of correcting or changing the measurement time ranges can be graphically and intuitively performed by using the pointing device, without entering numerical values by key operations.

After the measurement condition table 53 is appropriately corrected or modified, when the operator clicks the "Complete" button 55, the setting of the measurement condition table 53 is fixed, and a measurement condition file containing instructions for performing measurements as programmed in the table 53 is automatically created. Thus, the apparatus is ready for actual measurements of the unknown sample.

As described thus far, with the GC/MS according to the present embodiment, it is quite easy to define a measurement time range for performing a scan measurement, SIM measurement or simultaneous scan/SIM measurement, so that the operator's workload is reduced and input errors are prevented.

It should be obviously understood that the previous embodiment is a mere example and allows any changes, modifications or additions within the spirit and scope of the present invention.

The invention claimed is:

1. A chromatograph mass spectrometer having a chromatograph section in which sample components are separated in a temporal direction and a mass spectrometer section in which the sample components are sequentially subjected to a mass analysis, the mass spectrometer section being capable of selectively performing a scan measurement in which a mass-to-charge ratio is continuously and repeatedly scanned over a predetermined mass range, a selected ion monitoring (SIM) measurement in which the mass-to-charge ratio is switched from one value to another in a stepwise manner, with each value maintained for a specific period of time, or a simultaneous scan/SIM measurement in which the SIM measurement is performed in a course of the scan measurement, the chromatograph mass spectrometer comprising:
  a) a display controller showing a previously-created compound table on a screen of a display unit, the compound table including a list showing a kind of each compound, a normal retention time of each compound, and one or more mass-to-charge ratios characteristic of each compound;
  b) a selector for allowing an operator to select a compound that should undergo the simultaneous scan/SIM measurement, from the compound table displayed on the screen; and
  c) a measurement condition table creator producing a measurement condition table according to which the simultaneous scan/SIM measurement will be performed in a specified time range for each of one or more compounds selected by the selector and either the scan measurement or SIM measurement will be performed in other time ranges, the specified time range being defined for each of the selected compounds by setting a predetermined time span before and after the retention time of the compound, respectively.

2. The chromatograph mass spectrometer according to claim 1, wherein the display controller shows a total ion chromatogram obtained by a measurement of a standard sample or a known sample equivalent to the standard sample in a scan mode, SIM mode or simultaneous can/SIM mode, on the same screen on which the compound table and the measurement condition table are displayed.

3. The chromatograph mass spectrometer according to claim 2, wherein the display controller shows the total ion chromatogram in such a manner that one or more peaks present in the total ion chromatogram displayed on the screen are visually associated with one or more compounds listed in the compound table.

4. The chromatograph mass spectrometer according to claim 2, wherein the display controller superposes an indicator for visually identifying the time ranges of the scan measurement, SIM measurement and simultaneous scan/SIM measurement, on the total ion chromatogram displayed on the screen when the measurement condition table is created.

5. The chromatograph mass spectrometer according to claim 4, wherein the time range of the scan measurement, SIM measurement and simultaneous scan/SIM measurement can be graphically corrected through an operation of a pointing device.

6. The chromatograph mass spectrometer according to claim 1, wherein the selector provides the compound table with a check box for each compound in the compound table so that the operator can select a compound by checking an appropriate check box.

7. A method of operating a chromatograph mass spectrometer having a chromatograph section in which sample components are separated in a temporal direction and a mass spectrometer section in which the sample components are sequentially subjected to a mass analysis, the mass spectrometer section being capable of selectively performing a scan measurement in which a mass-to-charge ratio is continuously and repeatedly scanned over a predetermined mass range, a selected ion monitoring (SIM) measurement in which the mass-to-charge ratio is switched from one value to another in a stepwise manner, with each value maintained for a specific period of time, or a simultaneous scan/SIM measurement in which the SIM measurement is performed in a course of the scan measurement, the method comprising steps of:
  a) a display control process for showing a previously-created compound table on a screen of a display unit, the compound table including a list showing a kind of each compound, a normal retention time of each compound, and one or more mass-to-charge ratios characteristic of each compound;
  b) a selecting process for allowing an operator to select a compound that should undergo the simultaneous scan/SIM measurement, from the compound table displayed on the screen; and
  c) a measurement condition table creating process for producing a measurement condition table according to which the simultaneous scan/SIM measurement will be performed in a specified time range for each of one or more compounds selected by the selector and either the scan measurement or SIM measurement will be performed in other time ranges, the specified time range being defined for each of the selected compounds by setting a predetermined time span before and after the retention time of the compound, respectively.

8. The method of operating a chromatograph mass spectrometer according to claim 7, wherein, in the display control process, a total ion chromatogram obtained by a measurement of a standard sample or a known sample equivalent to the standard sample in a scan mode, SIM mode or simultaneous can/SIM mode is shown on the same screen on which the compound table and the measurement condition table are displayed.

9. The method of operating a chromatograph mass spectrometer according to claim 8, wherein the total ion chromatogram is shown in the display control process in such a manner that one or more peaks present in the total ion chromatogram displayed on the screen are visually associated with one or more compounds listed in the compound table.

10. The method of operating a chromatograph mass spectrometer according to claim 8, wherein an indicator for visually identifying the time ranges of the scan measurement, SIM measurement and simultaneous scan/SIM measurement is superposed on the total ion chromatogram displayed on the screen when the measurement condition table is created.

11. The method of operating a chromatograph mass spectrometer according to claim 10, wherein the time ranges of the scan measurement, SIM measurement and simultaneous scan/SIM measurement can be graphically corrected through an operation of a pointing device.

12. The method of operating a chromatograph mass spectrometer according to claim 7, wherein, in the selecting process, the compound table with a check box for each compound in the compound table is provided so that the operator can select a compound by checking an appropriate check box.

* * * * *